United States Patent
Moustafa

(10) Patent No.: US 12,383,591 B2
(45) Date of Patent: Aug. 12, 2025

(54) CHEWING GUM CONTAINING SYNERGISTIC MEDICINAL COMPOUNDS

(71) Applicant: LONDON PHARMACEUTICALS AND RESEARCH CORPORATION, London (CA)

(72) Inventor: Mahmoud Mohamed Abdrabo Moustafa, London (CA)

(73) Assignee: London Pharmaceuticals and Research Corporation, London (CA)

(*) Notice: Subject to any disclaimer, the term of this patent is extended or adjusted under 35 U.S.C. 154(b) by 485 days.

(21) Appl. No.: 17/776,366

(22) PCT Filed: Nov. 12, 2020

(86) PCT No.: PCT/CA2020/051530
§ 371 (c)(1),
(2) Date: May 12, 2022

(87) PCT Pub. No.: WO2021/092684
PCT Pub. Date: May 20, 2021

(65) Prior Publication Data
US 2023/0023342 A1  Jan. 26, 2023

Related U.S. Application Data

(60) Provisional application No. 62/934,061, filed on Nov. 12, 2019.

(51) Int. Cl.
*A61K 36/185* (2006.01)
*A61K 9/51* (2006.01)
*A61K 31/05* (2006.01)
*A61K 31/352* (2006.01)
*A61K 36/324* (2006.01)
*A61K 47/44* (2017.01)
*A61K 47/69* (2017.01)

(52) U.S. Cl.
CPC ............ *A61K 36/185* (2013.01); *A61K 9/51* (2013.01); *A61K 31/05* (2013.01); *A61K 31/352* (2013.01); *A61K 36/324* (2013.01); *A61K 47/44* (2013.01); *A61K 47/6935* (2017.08)

(58) Field of Classification Search
None
See application file for complete search history.

(56) References Cited

U.S. PATENT DOCUMENTS 10,004,684 B2    6/2018    Whittle et al.

FOREIGN PATENT DOCUMENTS

| GB | 2377633 A | 1/2003 |
| WO | 2005120478 A1 | 12/2005 |
| WO | 2007052013 A1 | 5/2007 |
| WO | 2008033024 A1 | 3/2008 |
| WO | 2009120080 A1 | 10/2009 |
| WO | 2017059859 A1 | 4/2017 |
| WO | 2017202424 A1 | 11/2017 |
| WO | 2019071213 A1 | 4/2019 |
| WO | 2020037408 A | 2/2020 |

*Primary Examiner* — Michael V Meller

(57) ABSTRACT

A medicinal chewing gum has an inner core containing a first gum base and a first cannabinoid in a lipophilic nano-sized form and an outer layer containing a second gum base and a second cannabinoid in a hydrophilic nanosized form, thereby providing quick release of the second cannabinoid in the outer layer and sustained release of the first cannabinoid in the inner layer. At least one of the inner core and the outer layer contains a synergistic compound having a synergistic effect with at least one of the first and second cannabinoids in the treatment of a medical condition.

12 Claims, 1 Drawing Sheet

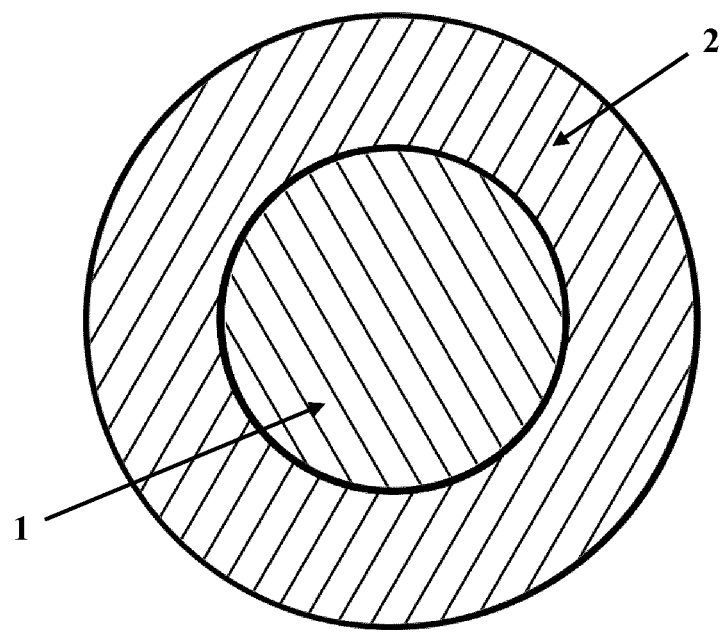

CHEWING GUM CONTAINING SYNERGISTIC MEDICINAL COMPOUNDS

FIELD OF THE INVENTION

The present invention relates to medicinal chewing gum compositions for the treatment of medical conditions and, in particular, to medicinal chewing gum containing a cannabinoid or a derivative thereof and other synergistic compounds for treatment or management of pain, inflammation, swelling, arthritis (osteoarthritis or rheumatoid arthritis), gout, lupus, anxiety, sleep disorders, premenstrual syndrome, asthma, respiratory and oral conditions, including infectious diseases (viral, bacterial, and fungal).

BACKGROUND

Cannabinoids are a heteromorphic group of compounds that modulate the endocannabinoid system with many attractive pharmacological actions. They can be classified into three main groups: a) endogenous or endocannabinoids e.g. arachidonoylethanolamide; b) natural or phytocannabinoids, which are the active constituents of *Cannabis* species (e.g. delta-9-tetrahydrocannabinol (THC) and cannabidiol (CBD)); c) synthetic (e.g. nabilone) (see Table 1).

TABLE 1

| Representative examples of cannabinoids |  |
|---|---|
| Cannabinoids class | Examples |
| A. Endogenous | Arachidonoylethanolamide |
| B. Natural | THC |
| | CBD |
| C. Synthetic | Nabilone |

The clinical utility of cannabinoids is well documented in many conditions, including chronic pain, inflammation, neurodegenerative disorders, epilepsy, addiction, insomnia, multiple sclerosis, cancer, obesity, and anorexia. Sativex®, by GW Pharmaceuticals, is a buccal spray of THC and CBD in a 1:1 mixture and has been approved in many countries as an adjunctive treatment of neuropathic pain and spasticity associated with multiple sclerosis in adults. Cesamet™ (nabilone), by Bausch Health Co, is a synthetic cannabinoid for oral administration as an antiemetic through a CB1 receptor mediated interaction.

Despite their clinical potential, natural cannabinoids (phytocannabinoids) are highly lipophilic (log P 6-7), sparingly soluble in water (solubility=2-10 μg/mL at 23° C.), chemically unstable (particularly in solution via light, temperature, and auto-oxidation), and gummy in nature with erratic absorption, a delayed onset, extensive first-pass metabolism, and low systemic bioavailability after oral administration. Moreover, the clinical benefits of smoked herb are short and associated with mucosal damage, serious adverse effects, and exposure to carcinogenic by-products.

A variety of formulations and administration methods have been developed in an attempt to overcome some of the limitations of ingested and smoked cannabinoids. Formulation strategies to increase solubility and stability of cannabinoids including derivatization, cosolvency, complexation, as well as surfactant and carrier-assisted methods.

When compared to other routes, drug delivery via the oral mucosa offers many advantages including bypassing first-pass metabolism, avoidance of GIT elimination and gastric acidity, fast onset of certain drugs due to rich blood supply, possibility of systemic and local delivery, convenience, and patient comfort/compliance. Furthermore, the oral mucosa is robust and tolerant to potential allergens. However, the oromucosal route is not suitable for all drugs due the distinctive characteristics of the oral mucosa, including its small surface area as well as its hydrophilic, hydrophobic and enzymatic barriers (e.g. estrases and peptidases). In addition, absorption via the oral mucosa is prone to lower bioavailability as well as high intra- and inter-subject variability.

Sativex®, by GW Pharmaceuticals, is a commercially available buccal spray of THC and CBD in a non aqueous 1:1 mixture of ethanol and propylene glycol to enhance solubility and permeation. It has been investigated for the treatment of arthritis (WO2005120478A1) and approved in many countries as an adjunctive treatment of neuropathic pain and spasticity associated with multiple sclerosis in adults (WO2007052013A1). Although designed for buccal absorption, Sativex® is reported to have a PK profile much like an oral preparation with a variable BA. This may be attributed to the dilution effect of the saliva and the reflex swallowing experienced by patients secondary to the non aqueous nature of the delivery system and the associated bad taste, mucosal irritation and hot stinging sensation (— 25% of patients). Furthermore, Sativex® is inherently prone to chemical instability and degradation because it is in solution form.

U.S. Pat. No. 10,004,684 B2 of GW Pharmaceuticals, discloses pharmaceutical formulations for use in the administration of lipophilic medicaments including cannabinoids via mucosal surfaces which, upon hydration, form an emulsion mass capable of adhering to the mucosal surface. Specific examples disclose a variety of forms including liquid, spray, disintegrating tablet, solid gel and soft gelatin capsule. However, this formulation allows only a limited degree of control over the particle size of the in-situ formed emulsion. Moreover, this system has intrinsic limitations, including susceptibility to microbial growth due to the use of carbohydrate based viscolising agents (carboxymethylcellulose, pre-gelatinised starch), irritation associated with chronic application, as well as a small surface and localized area for contact.

Another known delivery system, disclosed in WO 2008/033024 A2 of Echo pharmaceuticals B.V., is a self-emulsifying dispersible tablet for oromucosal delivery of water insoluble medications including cannabinoids. Although, the granules are obtained in the micron range (5-100 μM), the active ingredients are more prone to degradation during the micro-granulation process due to the use of high pressure and temperature.

Another known delivery system, disclosed in WO 2017/202424 A1 of Medcan Pharma A/S, is a granulated powdered composition comprising a complex between a cannabinoid and a basic ion exchange resin. Again, the active ingredients are more susceptible to degradation during the granulation process due to the use of temperature and/or aqueous solution.

Medicated chewing gum (MCG) is a modern solid dosage form for oromucosal drug delivery. It is used for the delivery of a number of active pharmaceutical ingredients, for example, nicotine, aspirin, dimenhydrinate, vitamins and antifungals. When compared to other oromucosal dosage forms (solutions, chewing tablets, adhesive forms, lozenges), MCG offers several advantages. It is a convenient ready-to-use unit dosage with better perception by patients. It can be used without water and taken at anytime and anywhere. It is a solid dosage form with better stability than many other dosage forms. The active ingredients can be protected from oxygen, light and water. It provides more control over bioavailability, permitting bypass of first pass metabolism, high BA, local and systemic effects, and has fewer adverse effects.

Despite their advantages in oromucosal drug delivery, MCG remains a niche dosage form due to limitations, including their complex formulation and production requirements, limited characterization and testing methods, and variable drug release due to differences in chewing pattern and rate.

A known chewing gum composition, disclosed in WO 2009/120080 A1 of Mare DA Holding BV, comprises 0.01 to 15% by weight a cannabinoid or a derivative thereof. During the preparation of this composition, degradation of THC was observed. Furthermore, the extraction of THC was not very efficient.

Another known chewing gum composition, disclosed in WO 2017/059859 A1 of Medcan Pharma A/S, comprises gum base polymers and one or more cannabinoids as an active pharmaceutical ingredient for pain alleviation. Other chewing gum preparations compromising cannabinoids with synergistic ingredients are also known, including, gingerol, *ginseng*, gabapentin, opioid agonists/antagonists and nicotine.

To minimize the limitations in the prior art, there exists a demand for a new delivery system that improves the pharmacokinetic/pharmacodynamic profile of cannabinoids.

SUMMARY OF THE INVENTION

A medicinal chewing gum, according to the present invention, has an inner core containing a first gum base and a first cannabinoid in a lipophilic nanosized form and an outer layer containing a second gum base and a second cannabinoid in a hydrophilic nanosized form, thereby providing quick release of the second cannabinoid in the outer layer and sustained release of the first cannabinoid in the inner layer. At least one of the inner core and the outer layer contains a synergistic compound having a synergistic effect with at least one of the first and second cannabinoids in the treatment of a medical condition.

In another embodiment, the first gum base of the inner core is a water-insoluble gum base polymer. The gum base polymer comprises polyisobutylene-polyethylene oxide (PIB-PEO) graft copolymers in an amount of 50-70% by weight of the gum base polymers, wherein the PIB-PEO graft copolymers include 2.5-40% by weight of PEO polymer.

In another embodiment, the cannabinoid is covalently attached through a biocompatible and biodegradable chemical bond and spacer to a PIB, PEO, or PIB-PEO graft copolymers.

In another embodiment, the PIB is crosslinked with another hydrophilic polymer. For example, the PIB may be crosslinked with polyethylene oxide, polyvinyl alcohol, polylysine or other polyaminoacids, hyaluronic acid, or chitosan.

In another embodiment, the outer layer contains the cannabinoid in a nanosized water-soluble form. The nanosized water-soluble form may include conjugates or complexes of the cannabinoid.

In another embodiment, the synergistic compound is a gum resin extract from *Boswellia* sp.

When compared to other conventional gum bases, the present invention may improve the PK and PD profile of cannabinoids, including achieving efficient release and better absorption. This may be attributed to the swelling and solubilization effects imparted by the PEO residues of the PIB-PEO gum base. In addition, the nanosized form of the cannabinoids increases solubility, stability and surface area of contact available for absorption, while improving their taste. Furthermore, the use of the natural gum resins from *Boswellia* sp. may have synergistic effects in treating medical conditions, such as pain and inflammation, and may further increase the swelling capacity of the gum and hence the bioavailability.

BRIEF DESCRIPTION OF THE DRAWINGS

In order that the invention may be more clearly understood, a preferred embodiment thereof will now be described in detail by way of example, with reference to the accompanying drawings, in which:

FIG. 1 is a cross-sectional view of a medicinal chewing gum, according to the present invention.

DESCRIPTION OF THE INVENTION

The term "nano-sized" in the present disclosure refers to nanoparticles, micelles, or liposomes with an average size between 20 nm and 200 nm. The nanosized forms may be hydrophilic, lipophilic, or amphiphilic based on their composition and preparation.

The term "cannabinoid" in the present disclosure refers to any of the group of chemical compounds that directly or indirectly act on the cannabinoid receptors of cells in a patient. They include numerous phytocannabinoids, such as those found in Cannabis sativa and other plants, and synthetic cannabinoids or endocannabinoids. Examples include, but are not limited to: delta-9-tetrahydrocannabinol (THC), delta-8-tetrahydrocannabinol (THC), cannabidiol (CBD), cannabinol (CBN), cannabinolic acid (CBNA), cannabigerol (CBG), cannabigerol (CBG), cannabigerovarin (CBGV), cannabichromene (CBC), cannabicyclol (CBL), canabivarol (CBV), tetrahydrocannabivarin (THCV), cannabidivarin (CBDV), cannabichromevarin (CBCV), cannabigerol monoethyl ether (CBGM), cannabigerolic acid monoethyl ether (CBGAM) cannabidiolic acid (CBDA), cannabigerovarinic (CBGVA), cannabichromenic acid (CBCA), cannabichromenic acid (CBCA), cannabidiol monomethylether (CBDM), cannabidiol-C4 (CBD-C4), cannabidivarinic (CBDVA), cannabidiorcol (CBD-C1), delta-9-tetrahydrocannabinolic acid A (THCA-A), delta-9-tetrahydrocannabinolic acid B (THCA-B), delta-9-tetrahydrocannabinolic acid-C4 (THCA-C4), delta-8-tetrahydrocannabinolic acid (delta-8-THCA), delta-8-tetrahydrocannabinol (delta-8-THC), delta-9-tetrahydrocannabinol-C4 (THC-C4), delta-9-tetrahydrocannabiorcolic acid (THCA-C1), delta-9-tetrahydrocannabiorcol-C1 (THC-C1), tetrahydrocannabivarinic acid (THCVA), cannabicycolic acid (CBLA), cannbicyclol (CBL), cannabicyclovarin (CBLV), cannabielsoic acid A (CBEA-A), cannabielsoic acid B (CBEA-B), cannabielsoin (CBE), cannabivarin, cannabinol-C4 (CBN-C4), cannabinol methylether (CBNM), cannabiorcol (CBN-C1), cannabinol-C2 (CBN-C2), cannabinodiol (CBND), cannabinodivarin (CBVD), cannabitriol (CBT), cannabitriolvarin (CBTV), dehydrocannabifuran (DCBF), cannabifuran, cannabicitran (CBT), cannabiripsol (CBR), '11-hy droxytetrahydrocannabinol' (11-OH-THC), '11-nor-9-carboxy-tetrahydrocannabinol' (THC-COOH), or their derivatives, synthetic analogues, or salts, or mixtures or combinations thereof.

The term "water-soluble cannabinoids" in the present disclosure refers to cannabinoid compounds that have been formulated, derivatized, or chemically synthesized in a water-soluble form including sulfate and hemi succinate esters of cannabinoids, or mixtures or combinations thereof.

The term "extract" in the present disclosure refers to compounds from plants that have been extracted and concentrated using one of the many known extraction methods, including solid-phase extraction (SPE), liquid-liquid extraction, ultrasonic and microwave-assisted extraction, heat and mechanochemical-assisted extraction, supercritical carbon dioxide extraction, and hydrocarbon and non-hydrocarbon solvent extracts.

The term "patient" in the present disclosure refers to human patients but is not limited to humans and may include other species.

The medicinal chewing gum, according to the present invention, provides an oromucosal delivery system for cannabinoids and synergistic compounds for the treatment of medical conditions, such as inflammation and pain, with an improved pharmacokinetic/pharmacodynamic profile, compared to some other forms of oral delivery of cannabinoids. The medicinal chewing gum provides both short-term quick release of cannabinoids and long-term sustained release of cannabinoids. This is useful in the treatment of medical conditions, such as inflammation and pain, to quickly alleviate symptoms and provide long-lasting relief to the patient.

The medicinal chewing gum contains active ingredients, synergistic ingredients, a gum base, and additives and fillers, and has an inner core 1 and an outer layer 2, as shown in FIG. 1. The active ingredients are one or more cannabinoid compounds, which may include: delta-9-tetrahydrocannabinol (THC), delta-8-tetrahydrocannabinol (THC), cannabidiol (CBD), cannabinol (CBN), cannabinolic acid (CBNA), cannabigerol (CBG), cannabigerol (CBG), cannabigerovarin (CBGV), cannabichromene (CBC), cannabicyclol (CBL), canabivarol (CBV), tetrahydrocannabivarin (THCV), cannabidivarin (CBDV), cannabichromevarin (CBCV), cannabigerol monoethyl ether (CBGM), cannabigerolic acid monoethyl ether (CBGAM) cannabidiolic acid (CBDA), cannabigerovarinic (CBGVA), cannabichromenic acid (CBCA), cannabichromenic acid (CBCA), cannabidiol monomethylether (CBDM), cannabidiol-C4 (CBD-C4), cannabidivarinic (CBDVA), cannabidiorcol (CBD-C1), delta-9-tetrahydrocannabinolic acid A (THCA-A), delta-9-tetrahydrocannabinolic acid B (THCA-B), delta-9-tetrahydrocannabinolic acid-C4 (THCA-C4), delta-8-tetrahydrocannabinolic acid (delta-8-THCA), delta-8-tetrahydrocannabinol (delta-8-THC), delta-9-tetrahydrocannabinol-C4 (THC-C4), delta-9-tetrahydrocannabiorcolic acid (THCA-C1), delta-9-tetrahydrocannabiorcol-C1 (THC-C1), tetrahydrocannabivarinic acid (THCVA), cannabicycolic acid (CBLA), cannbicyclol (CBL), cannabicyclovarin (CBLV), cannabielsoic acid A (CBEA-A), cannabielsoic acid B (CBEA-B), cannabielsoin (CBE), cannabivarin, cannabinol-C4 (CBN-C4), cannabinol methylether (CBNM), cannabiorcol (CBN-C1), cannabinol-C2 (CBN-C2), cannabinodiol (CBND), cannabinodivarin (CBVD), cannabitriol (CBT), cannabitriolvarin (CBTV), dehydrocannabifuran (DCBF), cannabifuran, cannabicitran (CBT), cannabiripsol (CBR), '11-hydroxytetrahydrocannabinol' (11-OH-THC), '11-nor-9-carboxy-tetrahydrocannabinol' (THC-COOH), or their derivatives, synthetic analogues, or salts, or mixtures or combinations thereof. Preferably, the cannabinoid compound is cannabidiol or tetrahydrocannabinol, or both, or their derivatives, synthetic analogues, or salts.

The active ingredients contained in the medicinal chewing gum are in a nanosized form, having a size of range between 20 nm and 200 nm. Preferably, in the range of 40-100 nm.

The synergistic ingredients are one or more phytochemicals effective in the treatment of inflammation or pain, which may include active isolates, extracts, or a gum base of: Boswellia sp., including Boswellia carterii and Boswellia serrata; ginger; capsaicin; camphor; polyphenols, including quercetin, ellagic acid, curcumin, and resveratrol; phytosterols; carbohydrates, including mannose-6-phosphate; essential oils, including thymol, and carvacrol; terpenoids, including squalene, lycopene, p-cymene, linalool, and carvacrol. Preferably, the phytochemical is a gum base of Boswellia sp., which has a dual purpose as both the gum base of the medicinal chewing gum and as a synergistic ingredient.

Where the synergistic ingredients are used in the form of a gum base, they may be provided as both the synergistic ingredients and the gum base of the medicinal chewing gum. Alternatively, one or more synergistic ingredients in the form of a gum base may be combined with another gum base in the medicinal chewing gum.

The gum base is a masticatory natural or synthetic gum base, which may include any of the synergistic ingredients described herein in the form of a gum base, and consist primarily of elastomers, resins, waxes, fats, and emulsifiers. Examples include, Gum Arabic, chicle and terpinene resins, beeswax, latex, paraffin, petroleum wax, hydrogenated soybean oil, glycerol monostearate, lecithin, polyethylene, polyvinyl alcohol, styrene-butadiene, polyisobutylene, or a polyisobutylene-polyethylene oxide (PIB-PEO) graft copolymer. The gum base could be hydrophilic, lipophilic, or amphiphilic. Preferably, the gum base is amphiphilic in nature and compromises a 1:1, 1:2 or 1:3 mixture of PIB-PEO and *Boswellia* resins. More preferably, the PIB-PEO to *Boswellia* resin ratio is 1:1. The PEO content of PIB-PEO could vary between 2.5%, 5%, 10%, 20%, 30%, and 40% (% wt). Preferably the PEO content of the PIB-PEO is 20-40% wt.

The PIB gum base may be crosslinked or non-crosslinked. Preferably, it is crosslinked with hydrophilic polymers, such as polyethylene oxide, hyaluronic acid (HA), chitosan, or polyaminoacids. The resulting crosslinked PIB gum base and hydrophilic polymers may provide improved biocompatibility, elasticity, and swelling capacity. In one exemplary embodiment, the PIB gum base may be crosslinked with HA, according to the formula below:

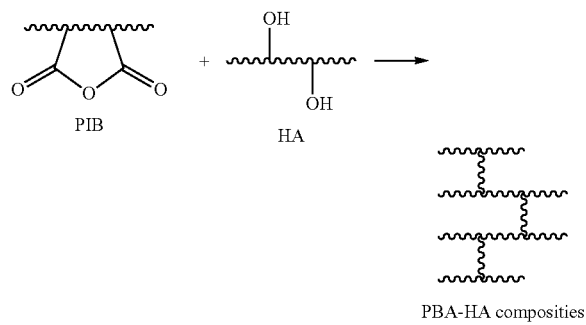

In some embodiments, the cannabinoids are physically entrapped within the gum base and are released as the gum is chewed by a patient. Alternatively, or additionally, the cannabinoids may be covalently attached to the polymer backbone of the gum base. Preferably, the gum base contains a mixture of physically entrapped cannabinoids, for relatively faster release and immediate effect, as well as covalently attached cannabinoids, for relatively slower release and sustained effect. In one exemplary embodiment, the cannabinoids may be covalently attached to a PIB gum base or a PIB-PEO gum base, according to the following formula:

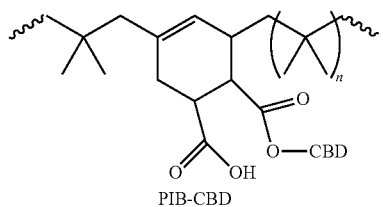

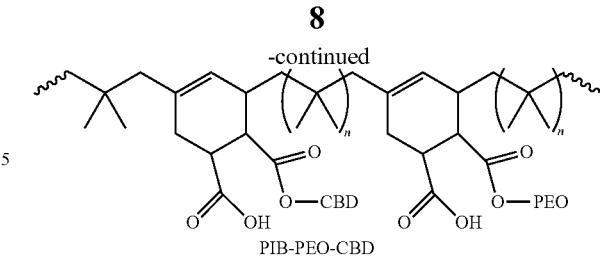

In some embodiments, where the gum base has both lipophilic and hydrophilic components, the cannabinoids may be covalently attached to the hydrophilic component of the gum base to increase the release of the cannabinoids during chewing of the gum by the patient. Preferably, the cannabinoids are covalently attached to the PEO component of a PIB-PEO gum base, before grafting the PEO to the PIB, which may also increase the loading of the cannabinoids on the gum base.

A number of non-masticatory additives and/or fillers are generally used in chewing gums, whether medicinal or otherwise, in order to provide a desired function and other characteristics of the chewing gum including texture regulating agents, fillers, and softeners, as well as stabilizing, flavouring, and sweetening agents. One or more additives or fillers are contained in the medicinal chewing gum to provide a desired set of characteristics to the chewing gum, which may include: waxes, sweeteners, flavours, colours, emulsifiers, antioxidants, stabilizers, buffers, enhancers, elastomers, plasticizers, water retention agents, thickening agents, ion exchange resins, or other suitable chewing gum additives and fillers. The ion exchange resins could be strongly or weekly basic. Preferably, the ion exchange resin is strongly basic, for example, poly (acrylamido-N-propylt-rimethylammonium chloride) (polyAPTAC).

The medicinal chewing gum has an inner core 1 and an outer layer 2. Each of the inner core 1 and the outer layer 2 contains the active ingredients, a gum base, and additives and fillers. At least one of the inner core 1 and outer layer 2 contains a synergistic ingredient, preferably both. The outer layer 2 differs from the inner core 1 at least in respect of the form in which the active ingredients are provided in each of the respective layers. The inner core 1 and outer layer 2 may also contain different or additional synergistic ingredients, gum bases, or additives and fillers. The active ingredients contained in the outer layer 2 are in the form of a hydrophilic or water-soluble preparation, while the active ingredients in the inner core 1 are in the form of a lipophilic preparation. Preferably, the outer layer 2 contains hydrophilic or water-soluble nanoparticles of one or more cannabinoids and the inner core 1 contains lipophilic nanoparticles one or more cannabinoids.

The lipophilic and gummy nature of cannabinoids makes them suitable candidates for advanced nanosized drug delivery methods. Nano sized cannabinoids may impart desirable properties including increased solubility, stability, surface area, and absorption. The synergistic ingredients may also be contained in the medicinal chewing gum in one or more nanosized forms. Where the synergistic ingredients are in the form of active isolates or extracts, they are combined with the active ingredients and nanoparticles are prepared with the combined ingredients. Preferably, the combined ingredients are used to prepare hydrophilic nanoparticles that are contained in the outer layer 2 and the combination is also used to prepare lipophilic nanoparticles that are contained in the inner core 1. The nanosized form could be lipid or solid nanoparticles as well as chelated or encapsulated systems. Preferably, lipid or solid nanoparticles have a size of between 20 nm and 200 nm. Preferably, in the range of 40-100 nm.

The hydrophilic active ingredients and/or synergistic ingredients in the outer layer 2 provide quick release of the active ingredients and/or synergistic ingredients as the patient initially begins chewing the medicinal chewing gum. This releases a portion of the active ingredients and/or synergistic ingredients substantially immediately to provide rapid onset of the relief of the patient's symptoms. Preferably, 50% of the active ingredients and/or synergistic ingredients in the outer layer 2 are released within 5 min of the patient beginning to chew the medicinal chewing gum.

The lipophilic active ingredients and/or synergistic ingredients in the inner core 1 provide controlled release of the active ingredients and/or synergistic ingredients as the patient continues chewing the medicinal chewing gum. This releases some or all the remaining active ingredients and/or synergistic ingredients over a prolonged period to provide long-lasting relief of the patient's symptoms. Preferably, 50% of the active ingredients and/or synergistic ingredients in the inner core 1 are released within 15-30 minutes of the patient chewing the medicinal chewing gum.

The additives and fillers contained in the inner core 1 may be the same or different from those contained in the outer layer 2, depending on the desired characteristics of each layer. The relative proportion of the additives and fillers may also be the same or different between the inner core 1 and outer layer 2. Preferably, 50-80% of sweeteners and flavouring agents are contained in the outer layer 2 in order to mask the taste and odor of the active ingredients.

Various synergistic effects of phytochemicals are known in the literature. In addition, extracts from *Boswellia* sp. are known to have an anti-inflammatory effect when administered to a patient on their own and are used as a natural chewing gum in many cultures and as anti-inflammatory ingredients in many natural health products. These extracts contain phytosterols with corticosteroid-like activity, however without adverse effects commonly seen with cortisones. They may further increase the swelling capacity of the gum and hence the bioavailability of the active ingredients. Also, they contain terpenoids, essential oils and phytosterols with pain-relief and anti-inflammatory effects. Finally, the natural gum base from *Boswellia* may increase the bioavailability of Cannabinoids because of the expected higher swelling capacity of the medicinal chewing gum. The gum base of a medicinal chewing gum, according to the present invention, may be amphiphilic in nature and may compromise a 1:1, 1:2 or 1:3 mixture of PIB-PEO and *Boswellia* resins. Preferably, the PIB-PEO to *Boswellia* resin ratio is 1:1.

General Methods for Making the Medicinal Chewing Gum

A medicinal chewing gum, according to the present invention, may be produced by known methods in the literature including a fusion method, cooling/grinding technology, and a direct compression approach. Preferably, the following steps are followed:

1. The gum base is softened or melted (at between 50-70° C.) and placed in a mixer.
2. Powdered ingredients and additives are then added and mixed.
3. The mixture is then cooled, rolled onto plates, and scored into strips to produce the lipophilic inner core (phase A).
4. Gum Arabic is dissolved in water and the water-soluble ingredients and additives, including sweeteners and flavouring agents, are then added and mixed to produce the hydrophilic outer layer (phase B).
5. The strips (from phase A) are then coated by the hydrophilic outer layer (from phase B).
6. The medicinal chewing gum is then dried and cut into pieces.

Gum Base Examples

According to one preferred embodiment of the present invention, the gum base comprises PIB and *Boswellia* extract in the % wt ratio of 100:0, 90:10, 80:20, 50:50, 20:80, or 0:100. In another embodiment, the gum base comprises PIB-PEO and *Boswellia* extract in the % wt ratio of 100:0, 90:10, 80:20, 50:50, or 20:80. In another embodiment, the gum base comprises PIB-CBD and *Boswellia* extract in the % wt ratio of 100:0, 90:10, 80:20, 50:50, or 20:80. In another embodiment, the gum base comprises PIB-PEO-CBD and *Boswellia* extract in the % wt ratio of 100:0, 90:10, 80:20, 50:50, or 20:80. In another embodiment, the gum base comprises PIB-HA and *Boswellia* extract in the % wt ratio of 100:0, 90:10, 80:20, 50:50, or 20:80.

Gum Base Example 1

An exemplary gum base comprising PIB-CBD or PIB-PEO-CBD may be prepared, according to the formula below, as follows:

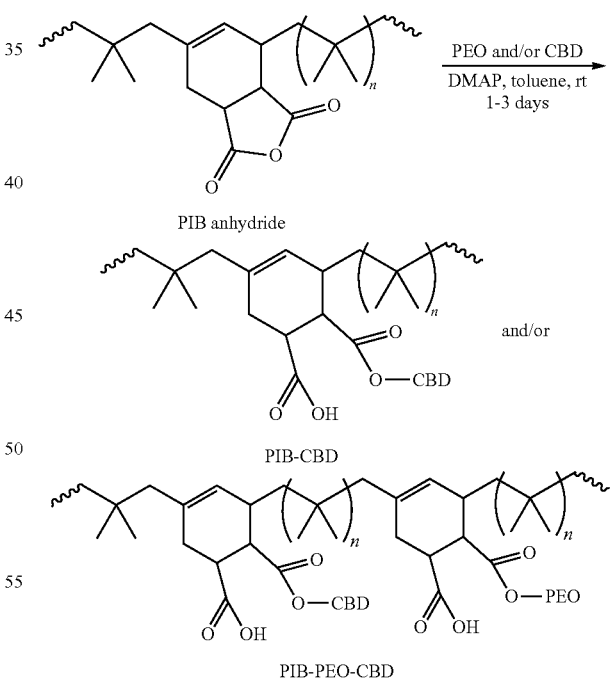

Add PIB anhydride (0.2 mmol of anhydride, 1.0 equiv.) to a solution of PEO or CBD, or both (0.4-1 mmol, 2-5 equiv.), and DMAP (0.6 mmol, 3 equiv.) in toluene (5-20.0 mL). Complete the reaction at room temperature for 1-3 days, then wash with HCl (1 M, 5 mL), water, and brine. Separate the organic layer and dry over anhydrous MgSO4, concentrate, and then precipitate in acetone (acetone:toluene 3:1).

Wash the resulting rubber with three 5 mL portions of acetone, and then dry in vacuo.

Gum Base Example 2

An exemplary gum base comprising PIB-HA may be prepared as follows. Add a solution of PIB anhydride (1.0 equiv.) in chloroform to a solution of HA (1 equiv.) and dimethoxy PEO (2K, 1 equiv.) in water. Sonicate the mixture using an ultrasonic probe to give a homogenous solution. Evaporate the solvents under vacuum to provide the final crosslinked PIB-HA gum base.

Chewing Gum Example 1

According to one preferred embodiment of the present invention, the medicinal chewing gum has the following composition.

| Gum Layer | Compound | Amount (% wt) |
|---|---|---|
| Inner core | PIB-PEO | 30% |
| | Boswellia resins | 30% |
| | Cannabinoids | 10% |
| | Additives | 5% |
| Outer shell | Gum Arabic | 10% |
| | Cannabinoids | 10% |
| | Additives | 5% |

The present invention has been described and illustrated with reference to an exemplary embodiment, however, it will be understood by those skilled in the art that various changes may be made and equivalents may be substituted for elements thereof without departing from the scope of the invention as set out in the following claims. Therefore, it is intended that the invention is not limited to the embodiments disclosed herein.

What is claimed is:

1. A medicinal chewing gum, comprising an inner core comprising polyisobutylene polyethylene oxide graft copolymer and cannabidiol in a lipophilic nanosized form and an outer layer comprising gum Arabic and cannabidiol in a hydrophilic nanosized form, wherein at least one of the inner core and the outer layer comprises a natural gum base of *Boswellia* sp.

2. The medicinal chewing gum of claim 1, wherein both the inner core and outer layer comprise a natural gum base of *Boswellia* sp.

3. The medicinal chewing gum of claim 2, wherein the polyethylene oxide content of the polyisobutylene-polyethylene oxide graft copolymer is between 2.5% wt. and 40% wt. and the ratio of the polyisobutylene-polyethylene oxide graft copolymer to the natural gum base of *Boswellia* sp. is between 1:1 and 1:3.

4. The medicinal chewing gum of claim 3, wherein the polyethylene oxide content of the polyisobutylene-polyethylene oxide graft copolymer is between 20% wt. and 40% wt. and the ratio of the polyisobutylene-polyethylene oxide graft copolymer to the natural gum base of *Boswellia* sp. is 1:1.

5. The medicinal chewing gum of claim 1, wherein at least a portion of the cannabidiol is covalently attached to at least one of the polyisobutylene polyethylene oxide graft copolymer, the gum Arabic, or the natural gum base of *Boswellia* sp.

6. The medicinal chewing gum of claim 5, wherein at least a portion of the cannabidiol is covalently attached to the polyethylene oxide before grafting the polyethylene oxide to the polyisobutylene.

7. A method of treating a medical condition in a human in need thereof, comprising:
   administering to the human in need thereof a medicinal chewing gum comprising an inner core comprising polyisobutylene polyethylene oxide graft copolymer and cannabidiol in a lipophilic nanosized form and an outer layer comprising gum Arabic and cannabidiol in a hydrophilic nanosized form, wherein at least one of the inner core and the outer layer comprises a natural gum base of *Boswellia* sp.; and
   wherein the medical condition is selected from the group consisting of pain, inflammation, swelling, osteoarthritis, rheumatoid arthritis, gout, lupus, anxiety, sleep disorders, premenstrual syndrome, asthma, respiratory infections and oral infections.

8. The method of claim 7, wherein both the inner core and outer layer comprise a natural gum base of *Boswellia* sp.

9. The method of claim 8, wherein the polyethylene oxide content of the polyisobutylene-polyethylene oxide graft copolymer is between 2.5% wt. and 40% wt. and the ratio of the polyisobutylene-polyethylene oxide graft copolymer to the natural gum base of *Boswellia* sp. is between 1:1 and 1:3.

10. The method of claim 9, wherein the polyethylene oxide content of the polyisobutylene-polyethylene oxide graft copolymer is between 20% wt. and 40% wt. and the ratio of the polyisobutylene-polyethylene oxide graft copolymer to the natural gum base of *Boswellia* sp. is 1:1.

11. The method of claim 7, wherein at least a portion of the cannabidiol is covalently attached to at least one of the polyisobutylene polyethylene oxide graft copolymer, the gum Arabic, or the natural gum base of *Boswellia* sp.

12. The method of claim 11, wherein at least a portion of the cannabidiol is covalently attached to the polyethylene oxide before grafting the polyethylene oxide to the polyisobutylene.

* * * * *